United States Patent
Pavlik

(10) Patent No.: US 9,186,493 B2
(45) Date of Patent: Nov. 17, 2015

(54) ASEPTIC CONNECTOR

(71) Applicant: ADVANCED SCIENTIFICS, INC., Millersburg, PA (US)

(72) Inventor: Rudolf Pavlik, Millersburg, PA (US)

(73) Assignee: Advanced Scientific, Inc., Millersburg, PA (US)

(*) Notice: Subject to any disclaimer, the term of this patent is extended or adjusted under 35 U.S.C. 154(b) by 0 days.

(21) Appl. No.: 14/476,900

(22) Filed: Sep. 4, 2014

(65) Prior Publication Data

US 2015/0290448 A1    Oct. 15, 2015

Related U.S. Application Data

(60) Provisional application No. 61/979,685, filed on Apr. 15, 2014.

(51) Int. Cl.
*A61M 39/00*    (2006.01)
*A61M 39/10*    (2006.01)
*A61M 39/18*    (2006.01)
*A61M 39/16*    (2006.01)

(52) U.S. Cl.
CPC .............. *A61M 39/10* (2013.01); *A61M 39/16* (2013.01); *A61M 39/18* (2013.01); *A61M 2039/1072* (2013.01)

(58) Field of Classification Search
CPC ..... A61M 39/18; A61M 39/22; A61M 39/10; A61M 2039/1077
See application file for complete search history.

(56) References Cited

U.S. PATENT DOCUMENTS

| 4,418,945 | A |   | 12/1983 | Kellogg |
| 5,590,782 | A | * | 1/1997 | Haber et al. .................. 206/528 |
| 5,713,850 | A | * | 2/1998 | Heilmann et al. .............. 604/28 |
| 5,810,398 | A |   | 9/1998 | Matkovich |
| 5,868,433 | A |   | 2/1999 | Matkovich |

(Continued)

FOREIGN PATENT DOCUMENTS

| EP | 1 574 200 A1 | 9/2005 |
| WO | 90/11103 | 10/1990 |

(Continued)

OTHER PUBLICATIONS

International Search Report and Written Opinion dated May 29, 2015, issued in PCT Application No. PCT/US2015/023980, filed Apr. 2, 2015.

*Primary Examiner* — Aarti B Berdichevsky
(74) *Attorney, Agent, or Firm* — Workman Nydegger

(57) ABSTRACT

An aseptic connector assembly and a method of aseptically transferring fluid are provided. The aseptic connector assembly includes a body portion, the body portion having a receptacle configured to receive a corresponding fill connector; a pivot portion adjustably disposed within and extending partially from the body portion, the pivot portion having a channel formed therein; and a conduit portion axially slidably disposed within the channel formed in the pivot portion. The pivot portion comprises a ready position and an operative position, the pivot portion being adjustable from the ready position to the operative position via relative movement with respect to the body portion. The method includes providing an aseptic connector in a ready position, coupling a flexible tubing and a fill connector to the aseptic connector, moving a pivot portion to an operative position, axially sliding the conduit portion into the fill connector, and transferring a fluid through the connector.

21 Claims, 4 Drawing Sheets

(56) References Cited

U.S. PATENT DOCUMENTS

| | | | |
|---|---|---|---|
| 6,238,372 B1 * | 5/2001 | Zinger et al. | 604/246 |
| 6,341,802 B1 | 1/2002 | Matkovich | |
| 6,485,483 B1 * | 11/2002 | Fujii | 604/535 |
| 6,536,805 B2 | 3/2003 | Matkovich | |
| 6,655,655 B1 | 12/2003 | Matkovich et al. | |
| 6,880,801 B2 | 4/2005 | Matkovich et al. | |
| 7,350,535 B2 * | 4/2008 | Liepold et al. | 137/68.19 |
| 2009/0229671 A1 * | 9/2009 | Hartnett et al. | 137/13 |
| 2010/0004619 A1 | 1/2010 | Rondeau et al. | |
| 2011/0087164 A1 * | 4/2011 | Mosler et al. | 604/87 |
| 2013/0105015 A1 * | 5/2013 | Deo et al. | 137/798 |
| 2013/0289517 A1 * | 10/2013 | Williams et al. | 604/500 |
| 2015/0028586 A1 * | 1/2015 | Gerst et al. | 285/352 |

FOREIGN PATENT DOCUMENTS

| | | |
|---|---|---|
| WO | 96/30076 | 10/1996 |
| WO | 2004/011077 A1 | 2/2004 |
| WO | 2008/111900 A1 | 9/2008 |
| WO | 2008/112275 A1 | 9/2008 |
| WO | 2012/114105 A1 | 8/2012 |

* cited by examiner

ASEPTIC CONNECTOR

CROSS-REFERENCE TO RELATED APPLICATIONS

This application claims priority to, and the benefit of, U.S. Provisional Patent Application No. 61/979,685, filed Apr. 15, 2014, entitled Aseptic Connector, which is hereby incorporated by reference in its entirety.

FIELD OF THE INVENTION

This invention relates to connectors for fluid transport and more particularly to a connector for the aseptic transfer of fluids from one location to another.

BACKGROUND OF THE INVENTION

Flexible containers are commonly used for containment and delivery of medical fluids. These containers are generally single use bags manufactured from one or more types of plastic film that can be irradiated or otherwise withstand sterilization such that the container can be rendered aseptic. The containers are often used in life science applications and in the manufacture of pharmaceuticals to contain liquid raw materials prior to or during manufacture; in other cases such containers may be used to contain the finished product. The contents of these containers may be precious, particularly when used in large scale production. It is not unusual for even small containers to contain material worth many thousands of dollars.

Furthermore, it is important that the fluids be capable of quick and efficient transfer between containers, such as from a large capacity container to smaller containers for sale or consumption, without compromising the sterility during transfer. The need to transfer fluids in sterile conditions introduces additional complications in keeping fluid within a controlled, sterile environment.

Various attempts have been made to deal with this issue and one system, the ASI Filling System commercially available from Advanced Scientifics, Inc. of Millersburg, Pa., can be used to yield an aseptic bag fill. The ASI Filling System is described in U.S. Pat. No. 7,530,374, which is incorporated herein by reference.

While this system presents a satisfactory solution for achieving an aseptically filled container, it is desirable to further enhance the functionality of this and other aseptic filling systems.

BRIEF DESCRIPTION OF THE INVENTION

Exemplary embodiments do so by providing a connector that can be used to subsequently evacuate those containers in an aseptic manner that accomplishes the filling and subsequent evacuation of the container via the same port, resulting in a more robust system.

In one embodiment, an aseptic connector assembly includes a body portion, the body portion having a receptacle configured to receive a corresponding fill connector; a pivot portion adjustably disposed within and extending partially from the body portion, the pivot portion having a channel formed therein; and a conduit portion axially slidably disposed within the channel formed in the pivot portion. The pivot portion comprises a ready position and an operative position, the pivot portion being adjustable from the ready position to the operative position via relative movement with respect to the body portion.

In another embodiment, a fluid transfer assembly includes the aseptic connector assembly, and a fluid container connected to the aseptic connector, the fluid container including a fill connector extending therefrom.

In another embodiment, a method of aseptically transferring fluid includes providing an aseptic connector in a ready position, the aseptic connector including a body portion, the body portion having a receptacle configured to receive a corresponding fill connector, a pivot portion adjustably disposed within and extending partially from the body portion, the pivot portion having a channel formed therein, and a conduit portion axially slidably disposed within the channel formed in the pivot portion; coupling a flexible tubing to the conduit portion; coupling the fill connector to the receptacle; moving the pivot portion to an operative position and aligning the conduit portion with the receptacle; axially sliding the conduit portion into an opening in the receptacle, establishing a continuous fluid flow path through the aseptic connector; and transferring a fluid from a fluid source, through the aseptic connector, to a container.

An advantage of exemplary embodiments is that fluids can be aseptically transferred without sterilizing an exterior of a container from which the fluids are being transferred.

Another advantage is that rotation of the aseptic connector removes a cap from a fill connector of a container and exposes a septum, the septum providing a secondary barrier to the environment.

Yet another advantage is that after removing the evacuated container, the aseptic connector maintains the sterility of the tube and/or container to which the fluids were transferred.

A further advantage is that the aseptic connector includes a stop to prevent repeated use of the aseptic connector after the evacuated container has been removed.

Other features and advantages of the present invention will be apparent from the following more detailed description of exemplary embodiments that illustrate, by way of example, the principles of the invention.

BRIEF DESCRIPTION OF THE DRAWINGS

Wherever possible, the same reference numbers will be used throughout the drawings to represent the same parts.

DETAILED DESCRIPTION OF THE INVENTION

Figure 1:
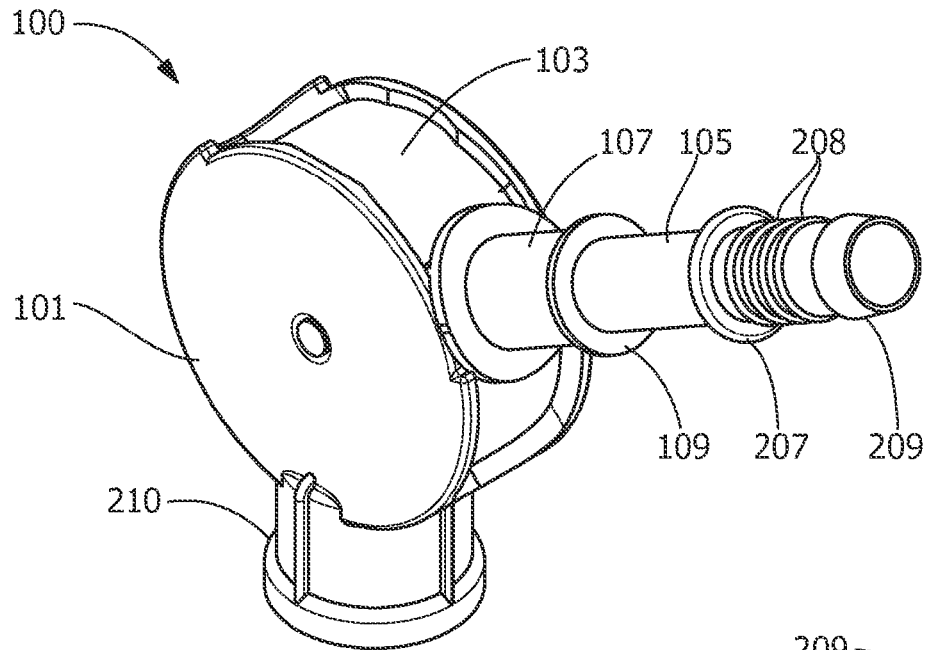
FIG. 1 is a perspective view of an aseptic connector, according to an embodiment of the disclosure.
Figure 2:
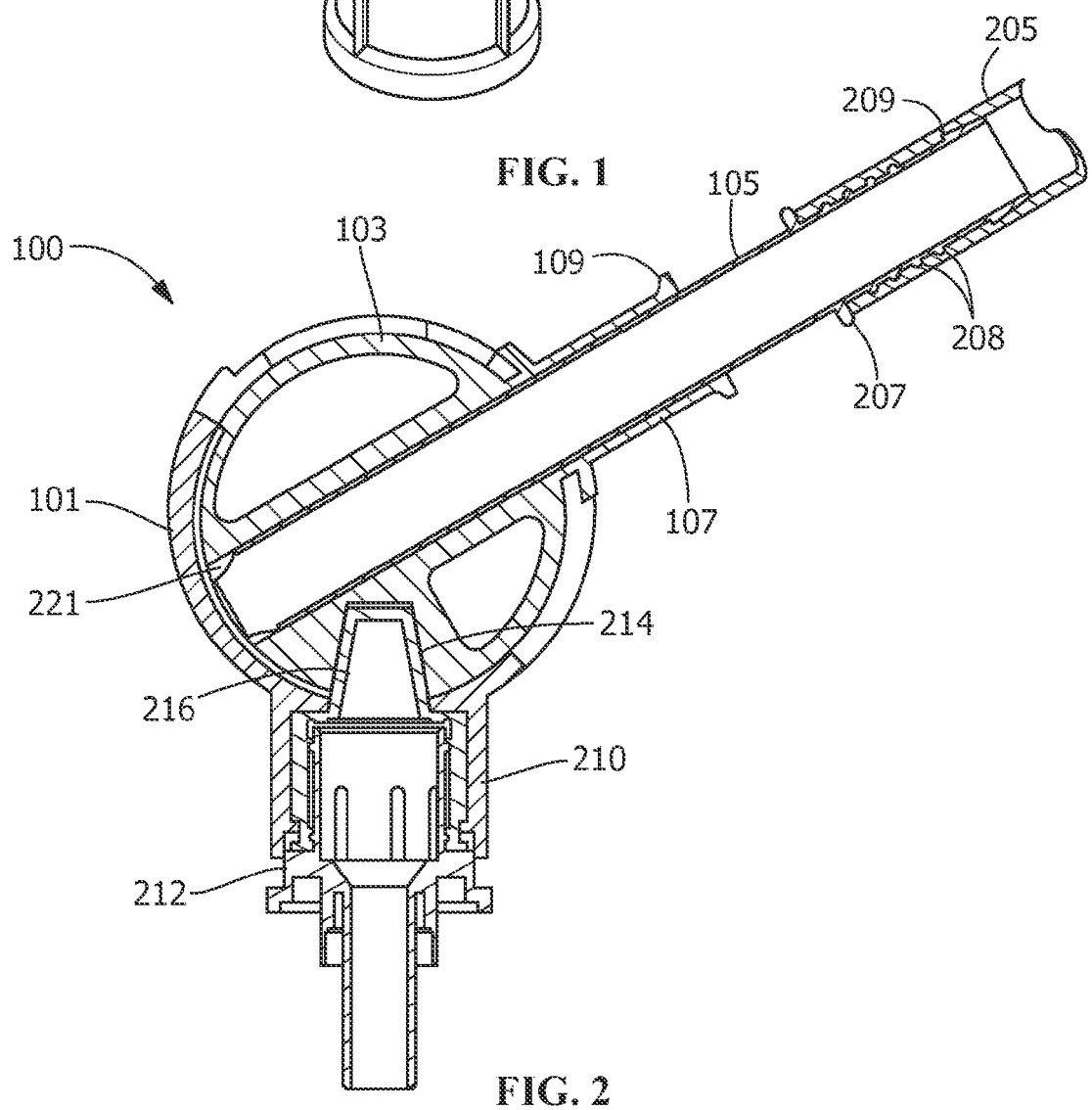
FIG. 2 is a cross-sectional view of the aseptic connector of FIG. 1.

Referring to FIGS. 1 and 2, an aseptic connector 100 includes a body portion 101, a pivot portion 103, and a conduit portion 105. The conduit portion 105 is axially slidably disposed within a channel 107 formed in the pivot portion 103. In one embodiment, the pivot portion 103 is adjustably disposed within, and partially extends from, the body portion 101. A thin layer of a soft, sealing material may be disposed intermediate a region of the outer surface of the pivot portion 103 and the inner surface of the body portion 101 to act as a seal, preventing leaks and maintaining sterility. This and other seals are optionally included within the connector as desired.

In one embodiment, the aseptic connector 100 is pivotable in a single direction, transitioning from a ready position (as shown in FIG. 1), to an active position (i.e., fill/evacuate position) and from that position to a closed position as will be described in more detail subsequently. In another embodiment, the body portion 101 may be configured with travel stops to establish a range of motion for the pivot portion 103 between the ready, active, and/or closed positions, defining single directional movement between positions and preventing over or under rotation. The travel stops may further provide a palpable signal to the user that the aseptic connector 100 is in the proper position. In a further embodiment, the aseptic connector 100 is a single use aseptic connector, including a feature for preventing re-use of the aseptic connector 100 for another connection after removal.

The aseptic connector 100 may be formed from any material suitable for sterilization. Suitable materials include, but are not limited to, plastic resins, preferably those selected from grades suitable for medical and/or life science use (e.g., materials class VI) and which are also resistant to high temperatures and gamma radiation to permit steam and/or gamma sterilization procedures that render the aseptic connector sterile prior to use. In one embodiment, sterilization of the aseptic connector 100 may be accomplished through autoclave sterilization at 270° F. (132° C.) for 60 minutes. In another embodiment, the aseptic connector 100 is resistant to up to 25 or more repetitions of the sterilization. Other embodiments include sterilization through gamma irradiation, e-beam sterilization, EtO sterilization, or a combination thereof. For gamma irradiation and/or e-beam sterilization, the aseptic connector 100 is resistant to a maximum cumulative exposure of up to 50 Kilograys. For EtO sterilization, the aseptic connector 100 is resistant to 100% EtO at 110° F. (43° C.) for up to five repetitions. It will be appreciated that sterilization should be done in an uncoupled position.

As illustrated in FIG. 2, the conduit portion 105, which is shown as a male connection, is connected to flexible tubing 205 to extend the fluid flow path to some other container or other location to which the fluid is to be delivered. The conduit portion 105 may include a raised wall 207 to provide a travel stop, the travel stop establishing an appropriate overlap length of the tubing 205. The conduit portion 105 may also include one or more raised ribs 208 and/or a flared outlet 209 to aid in retaining the tubing 205 securely on the conduit portion 105 during use. Additionally, the one or more raised ribs 208 and/or the flared outlet 209 reduce the possibility of leaking that would thereby compromise the aseptic nature of the fluid path.

The aseptic connector 100 also includes a receptacle 210 formed in the body portion 101. The receptacle 210 is configured to receive a fill connector 212 appended to a fluid source, such as a filled flexible container or other suitable container 301 (see FIG. 3) from which liquid is to be aseptically evacuated. For example, in one embodiment, the aseptic connector 100 includes a female receptacle configured to receive a male fill connector of the container 301, thus connecting the aseptic connector 100 to the container 301. In another embodiment, receptacle 210 of the aseptic connector 100 directly connects with the fill connector 212 through any suitable connection mechanism. Suitable connection mechanisms include, but are not limited to, a threaded connection, a trapezoid thread on the outer diameter of the fill connector 212, a locking or snapping connection, or a combination thereof. In a preferred embodiment, the fill connector 212 is of the type described in U.S. Pat. No. 7,530,374 and/or those used in the flexible containers sold by Advanced Scientifics of Millersburg, Pa. which are adapted to interface with attachments.

In the ready configuration shown in FIG. 2, a recess 214 in the pivot portion 103 is aligned with receptacle 210. The recess 214 is configured to receive a cap 216 of the fill connector 212 when the fill connector 212 is attached to the receptacle 210, and the aseptic connector 100 in the ready position. Together, the aseptic connector 100, the fill connector 212 attached to the receptacle 210, and the container 301 extending from the fill connector 212 form a fluid transfer assembly. Even with the aseptic connector 100 secured in its position along the fluid flow path, the body portion 101 is not in fluid communication with the conduit portion 105 when the aseptic connector 100 is in the ready position. As body portion 101 is not in fluid communication with the conduit portion 105, the flexible container 301 is not in fluid communication with the flexible tubing 205 for the flow of liquid content therethrough.

Figure 3:
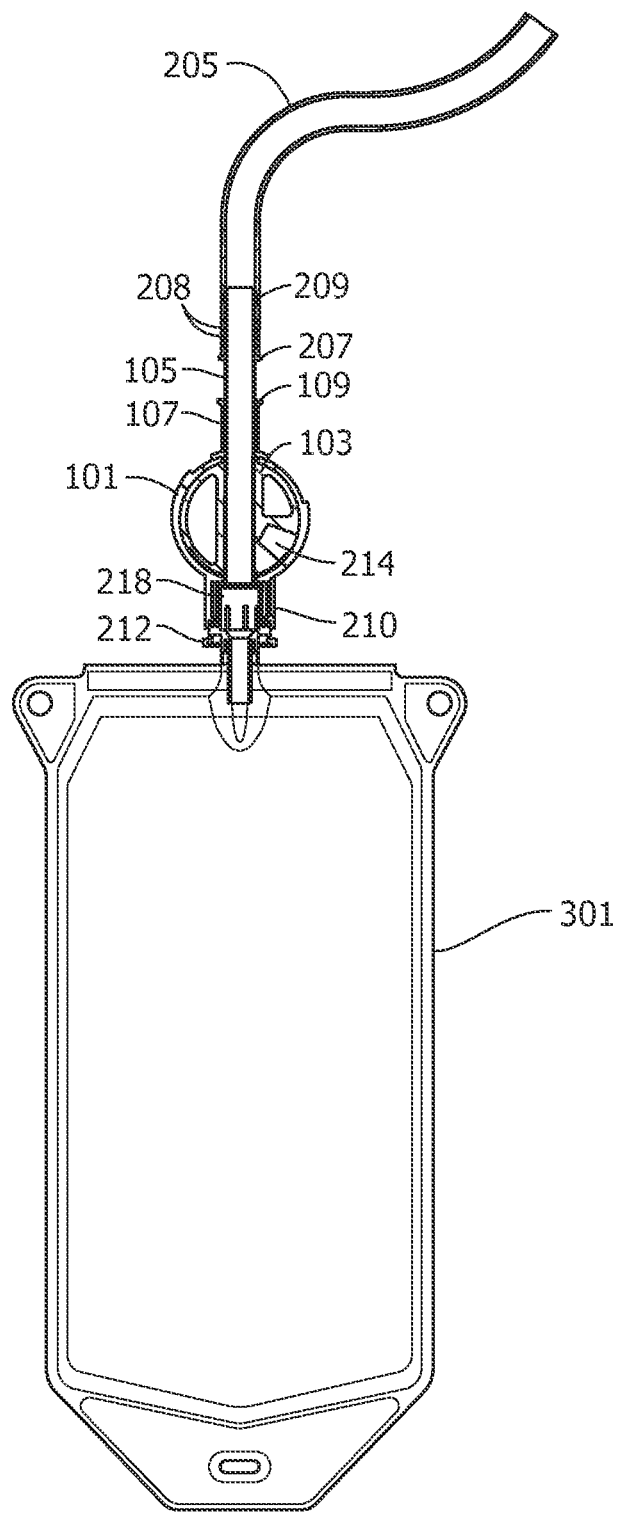
FIG. 3 is a perspective view of an aseptic connector attached between a flexible container and flexible tubing.

Referring to FIG. 3, the aseptic connector 100 is shown in its active, evacuate position, in which the pivot portion 103 is rotated into a position that aligns the conduit portion 105 residing in the channel 107 of the pivot portion 103 with the opening in the female receptacle 210. The aligning of the conduit portion 105 with the female receptacle 210 also aligns the conduit portion 105 with the fill connector 212 attached thereto. In addition, the rotation of the pivot portion 103 from the ready to the active position breaks the fill connector cap 216 away from the fill connector 212. In one embodiment, for example, the rotation of the pivot portion 103 disengages the cap 216 with ten pounds of force or less. The breaking away of the cap 216 exposes a septum 218 in the fill connector 212 as a secondary barrier to the environment. Because this interface of the aseptic connector 100 and fill connector 212 was not exposed to the environment, it remains a sterile portion of a closed pathway.

After the aseptic connector 100 has been placed in the active position, and the conduit portion 105 is aligned with the receptacle 210, the conduit portion 105 can be moved axially into the fill connector 212. A taper 221 (see FIG. 2) or spike may be formed at the proximal end of the conduit portion 105 to more easily penetrate any septum 218 that underlies the cap 216 of the fill connector 212. In one embodiment, the wall 207 on the outer diameter of the conduit portion 105 is conveniently used to also establish the proper penetration depth of the conduit portion 105 through the body portion 101 into the fill connector 212. For example, the wall 207 on the conduit portion 105 may establish the proper penetration depth by contacting a complementary wall 109 (see FIGS. 1 and 2) of an extension of the pivot portion 103. In addition to or in place of the wall 207, any other mechanism by which the depth of the conduit portion 105 into the fill connector 212 can be controlled may be used. A mechanical stop may also be employed in the pivot portion 103 and/or the conduit portion 105 to prevent the conduit portion's 105 unintentional removal from the aseptic connector 100 (for example, when retracting the conduit portion from the fill connector after use).

Once the conduit portion 105 has been moved axially into the fill connector 212 and/or the septum 218 is penetrated, a continuous fluid flow path is established through the aseptic connector 100 between the flexible container 301 and the flexible tubing 205. The continuous fluid flow path permits aseptic evacuation of the contents of the flexible container 301 through the aseptic connector 100 and flexible tubing 205 to another location. According to exemplary embodiments, the aseptic connector 100 provides for aseptic fill and evacuation at pressures of up to 125 psi (8.6 bar), and temperatures of between −40° F. (−40° C.) and 280° F. (138° C.), although greater pressures and temperatures are possible.

After the transfer is completed, the conduit portion 105 is retracted. The pivot portion 103 is rotated another step to the closed position, which is the final position of the aseptic connector 100. To assure sterility, once moved to the closed position, the pivot portion 103 cannot be returned to the active position. That is, it is locked in place and an operator cannot move the pivot portion 103 relative to the body portion 101.

At this point, the aseptic connector 100 can be detached from the fill connector 212 (typically by unscrewing when using the preferred threaded connection). The aseptic connector 100, or at least that portion of it including the conduit portion 105, having been transitioned to its closed position prior to removing the fill connector 212, remains sterile. While the fill connector side (i.e. the female receptacle of the base portion) is considered jeopardized by exposure to the environment following removal from the body portion 101, the closed position seals that exposure from the interior of the aseptic connector 100, including the conduit portion 105. Furthermore, the contents of the flexible container 301 are presumably evacuated to the extent desired (preferably until empty in most instances) and the sterility of the disconnected fill connector 212 itself at that point is also of little concern.

Figure 4:
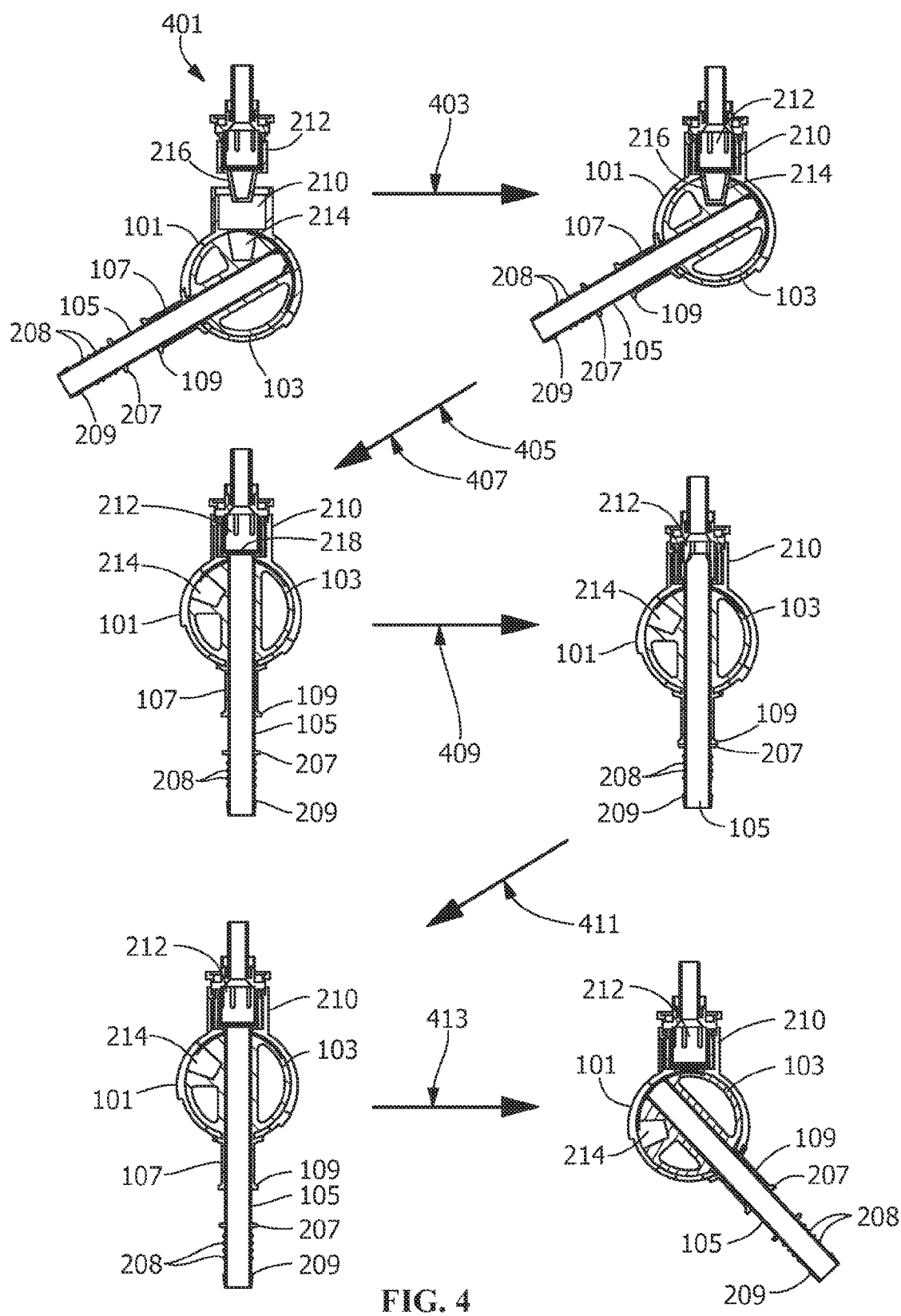
FIG. 4 is a schematic view of the operation of an aseptic connector.

Referring to FIG. 4, a method of operating the aseptic connector 100 includes, aligning the fill connector 212 of the flexible (or other style of) container housing liquid contents to be aseptically evacuated with the receptacle 210 of the aseptic connector body portion 101 (step 401). The aligning of the fill connector 212 with the receptacle 210 is performed with the aseptic connector 100 staged in the ready position. The fill connector 212 is then fully secured to the receptacle 210 of the aseptic connector 100 (step 403). As illustrated in FIG. 4, the connector 212 is screwed onto the receptacle 210, although any other securing mechanism may be used. After securing the fill connector 212 to the receptacle 210, the fill connector cap 216 is seated within the recess in the pivot portion 103 of the aseptic connector 100.

Next, the pivot portion 103 is rotated into the active position (step 405), breaking off the fill connector cap 216. As illustrated, the body portion 101 includes a side opening that allows the cap 216 to be ejected (step 407) from the aseptic connector 100 after being broken off of the fill connector 212. After rotating the pivot portion 103 into the active position, the conduit portion 105 is axially slid into the fill connector 212 in the receptacle 210 (step 409), piercing any septum in the fill connector 212, and establishing fluid communication through the aseptic connector 100 to evacuate the contents of the flexible container 301.

After evacuation is complete, the conduit portion 105 is retracted from the fill connector 212 (step 411) and the pivot portion 103 is rotated another increment to a closed position (step 413), closing the flow path on the conduit portion side, and permitting the subsequent removal of the now-evacuated flexible container 301 for disposal, while retaining the aseptic flowpath from the aseptic connector 100 to the flowpath's terminus.

As a result, the aseptic connector 100 of the invention, when used in conjunction with a sterile fill system such as the one described, provides a system that allows fill and evacuation aseptically through the same port of a flexible container 301. In a preferred embodiment, the aseptic connector meets compliance specifications for one or more of the following: ISO 10993, NAO, Cytotoxity, and is BPA, DEHP, Latex and/or Melamine free. Furthermore, in a preferred embodiment, the aseptic connector is capable of meeting some or all of the following tests, the procedures for which are known to those of ordinary skill in the art: Bacterial Challenge, Microbial Ingress Test, Steam Leak Test, Helium Leak Test, Burst Test, Flow Test, Tensile Test, Creep-Rupture Test, Biocompatibility Tests, Functional Testing after Accelerated Aging, Bubble Leak Test, Endotoxin Test, Bioburden Test, and Total Organic Compounds (TOC).

Figure 5:
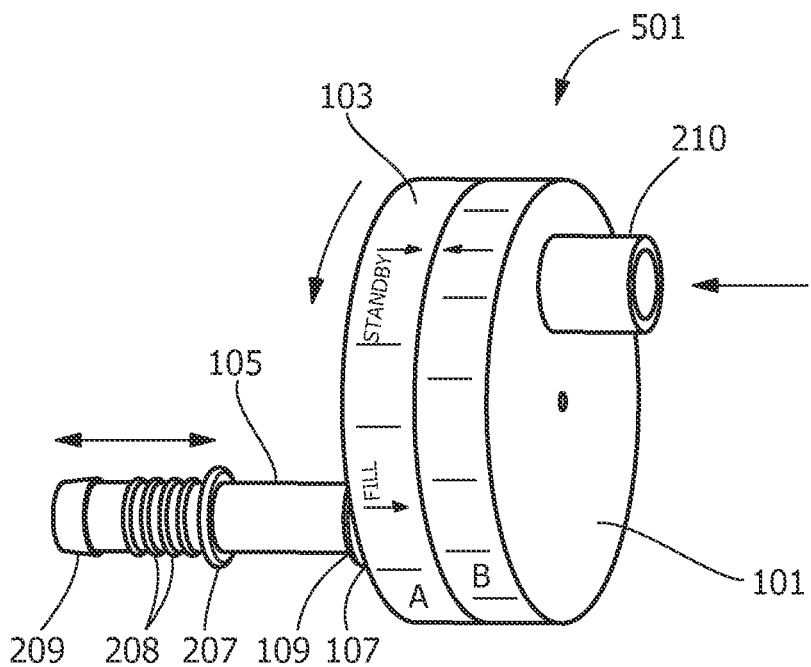
FIG. 5 is a perspective view of a dial type aseptic connector, according to an embodiment of the disclosure.
Figure 6:
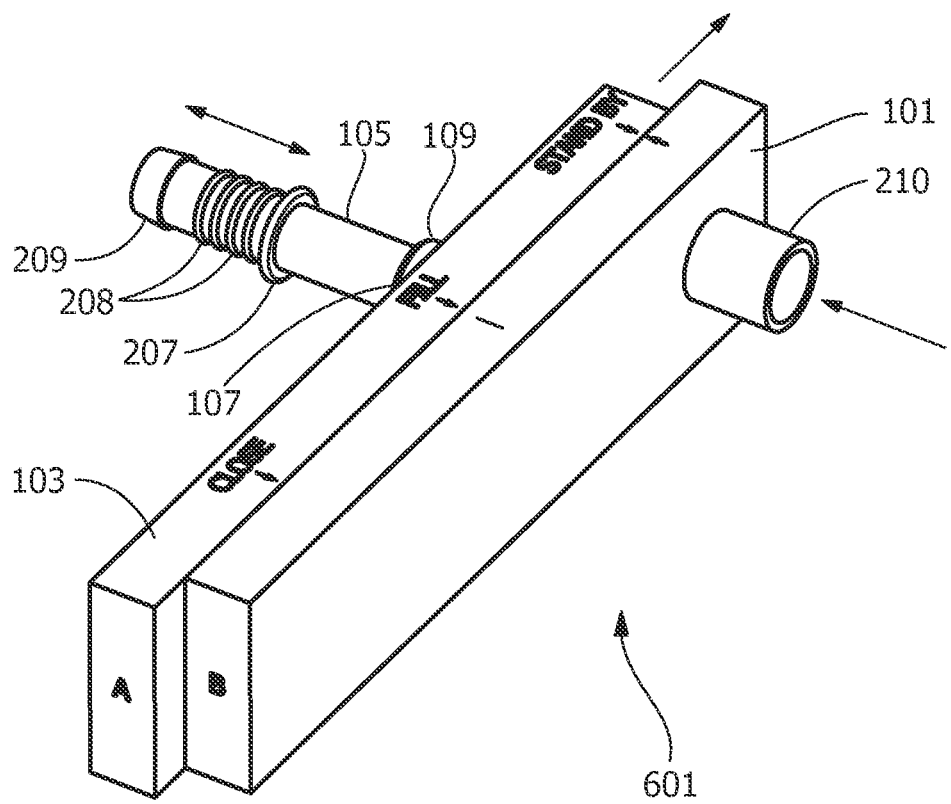
FIG. 6 is a perspective view of a sliding type aseptic connector, according to an embodiment of the disclosure.

Alternative embodiments are shown in FIGS. 5 and 6, which illustrate other mechanical arrangements that demonstrate an aseptic connector 100 having one-directional advancement from ready to active to closed positions. FIG. 5 illustrates a dial type connector 501, while FIG. 6 illustrates a sliding type connector 601. While the manner in which relative movement of the body portion 101 with respect to the pivot portion 103 is different, the effect is the same as described previously, with the receptacle 210 receiving the fill connector 212, moving the pivot portion 103 with respect to the body portion 101 to align the conduit portion 105 and/or spike and pierce the septum 218 (see FIGS. 3-4) to permit fluid flow, followed by again moving the pivot portion 103 with respect to the body portion 101 to close the fluid flow path to permit separation of the container 301 without loss of sterility to the opposite end of the flow path. It will be appreciated that other mechanical arrangements are also contemplated that fall within the concept of the invention of providing an aseptic connector that mates with a fill connector of a container and thus permits sterile filling and evacuation of the container by the same port.

It will be appreciated that the references to fill connector and aseptic connector as used herein is primarily for purposes of differentiating mechanical parts and while named with respect to the convention of a preferred embodiment, is not intended as a limitation on use or to define the direction in which fluid necessarily flows.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A fluid transfer system, comprising:
   an aseptic connector assembly, comprising:
     a body portion, the body portion having a receptacle therein,
     a pivot portion at least partially disposed within the body portion, the pivot portion having a channel formed therein and a recess formed therein,
     wherein the pivot portion comprises a ready position and an operative position, the pivot portion being adjustable from the ready position to the operative position via relative movement with respect to the body portion, and
     a conduit portion axially slidably disposed within the channel formed in the pivot portion;
   a fluid container; and
   a fill connector extending from the fluid container and having a frangible cap, the fill connector being connected to the receptacle of the body portion, wherein the recess of the pivot portion is arranged and disposed to receive the frangible cap of the fill connector when the pivot portion is in the ready position.

2. The fluid transfer system of claim 1, wherein the aseptic connector assembly is configured to remove the frangible cap in a transition from the ready position to the operative position.

3. The fluid transfer system of claim 1, wherein the recess is aligned with and in communication with the receptacle when the pivot portion is in the ready position.

4. The fluid transfer system of claim 1, wherein the fill connector includes a septum at least partially covered by the frangible cap.

5. The fluid transfer system of claim 1, wherein the conduit portion is aligned with the receptacle when the pivot portion is in the operative position.

6. An aseptic connector assembly, comprising:
 a body portion, the body portion having a receptacle configured to receive a corresponding fill connector;
 a pivot portion at least partially disposed within the body portion, the pivot portion having a channel formed therein and a recess formed therein, wherein the pivot portion comprises a ready position and an operative position, the pivot portion being adjustable from the ready position to the operative position via relative movement with respect to the body portion, the recess being aligned with and in communication with the receptacle when the pivot portion is in the ready position, the channel being aligned with the receptacle when the pivot portion is in the operative position; and
 a conduit portion axially slidably disposed within the channel formed in the pivot portion.

7. The aseptic connector assembly of claim 6, wherein the receptacle is a female receptacle and the corresponding fill connector is a male fill connector.

8. The aseptic connector assembly of claim 6, wherein the pivot portion further comprises a closed position, the pivot portion being adjustable from the operative position to the closed position via relative movement with respect to the body portion.

9. The aseptic connector assembly of claim 6, wherein the relative movement of the pivot portion comprises sliding or rotating the pivot portion with respect to the body portion.

10. The aseptic connector assembly of claim 6, wherein the recess is offset from and not in communication with the receptacle when the pivot portion is in the operative position.

11. The aseptic connector assembly of claim 6, wherein, in the ready position, the conduit portion and the body portion are not in fluid communication with one another.

12. The aseptic connector assembly of claim 11, wherein, in the operative position, the conduit portion is axially slidably extendable into the receptacle thereby placing the body portion in fluid communication with the conduit portion.

13. The aseptic connector assembly of claim 6, wherein the conduit portion further comprises a raised wall.

14. The aseptic connector assembly of claim 13, wherein the raised wall provides a travel stop for axial movement of the conduit portion within the channel, and defines an overlap length of a tubing connected to the conduit portion.

15. The aseptic connector assembly of claim 6, wherein a proximal end of the conduit portion is arranged and disposed to penetrate a septum in the fill connector when the pivot portion is in the operative position.

16. The aseptic connector assembly of claim 15, further comprising a septum penetrating member formed on the proximal end of the conduit portion, the septum penetrating member being selected from the group consisting of a taper, a spike, and combinations thereof.

17. A fluid transfer assembly, comprising:
 the aseptic connector assembly of claim 6; and
 a fluid container connected to the aseptic connector, the fluid container including a fill connector extending therefrom.

18. The fluid transfer assembly of claim 17, wherein the fill connector extending from the fluid container is connected to the receptacle of the body portion.

19. The fluid transfer assembly of claim 18, wherein the fill connector includes a frangible cap.

20. The fluid transfer assembly of claim 19, wherein the recess is arranged and disposed to receive the frangible cap of the fill connector when the pivot portion is in the ready position.

21. The fluid transfer assembly of claim 20, wherein the aseptic connector assembly is configured to remove the frangible cap from the fill connector in a transition from the ready position to the operative position.

* * * * *